United States Patent
Lim et al.

(10) Patent No.: US 11,951,089 B2
(45) Date of Patent: Apr. 9, 2024

(54) PHARMACEUTICAL COMPOSITION FOR PREVENTING OR TREATING WOUND OR SCAR, COMPRISING BENZBROMARONE

(71) Applicant: INNOVO THERAPEUTICS INC., Seoul (KR)

(72) Inventors: Dong Chul Lim, Daejeon (KR); Jung Gyu Park, Daejeon (KR)

(73) Assignee: INNOVO THERAPEUTICS INC., Seoul (KR)

( * ) Notice: Subject to any disclaimer, the term of this patent is extended or adjusted under 35 U.S.C. 154(b) by 0 days.

(21) Appl. No.: 18/254,211

(22) PCT Filed: Nov. 29, 2021

(86) PCT No.: PCT/KR2021/017723
§ 371 (c)(1),
(2) Date: May 24, 2023

(87) PCT Pub. No.: WO2022/114881
PCT Pub. Date: Jun. 2, 2022

(65) Prior Publication Data
US 2023/0390236 A1    Dec. 7, 2023

(30) Foreign Application Priority Data
Nov. 30, 2020 (KR) .................. 10-2020-0163975

(51) Int. Cl.
*A61K 31/343* (2006.01)
*A61P 17/02* (2006.01)

(52) U.S. Cl.
CPC ............ *A61K 31/343* (2013.01); *A61P 17/02* (2018.01)

(58) Field of Classification Search
CPC ............................. A61K 31/343; A61P 17/02
USPC ........................................................ 514/469
See application file for complete search history.

(56) References Cited

U.S. PATENT DOCUMENTS

2010/0093613 A1    4/2010  Kunkel et al.
2017/0314021 A1   11/2017  Ayabe et al.

FOREIGN PATENT DOCUMENTS

| CN | 105837532 A | 8/2016 |
|---|---|---|
| EP | 0 742 012 A2 | 11/1996 |
| EP | 2 165 705 A1 | 3/2010 |
| JP | 8-301781 A | 11/1996 |
| KR | 10-2012-0120931 A | 11/2012 |
| WO | 98/50033 A1 | 11/1998 |
| WO | 02/060896 A1 | 8/2002 |
| WO | 2005/013947 A2 | 2/2005 |
| WO | 2008/012511 A1 | 1/2008 |

(Continued)

OTHER PUBLICATIONS

Ito et al., "A small-molecule compound inhibits a collagen-specific molecular chaperone and could represent a potential remedy for fibrosis", J. Biol. Chem., 2017, 292(49): 20076-20085.

(Continued)

*Primary Examiner* — Taylor V Oh
(74) *Attorney, Agent, or Firm* — Vorys, Sater, Seymour and Pease LLP; Mih Suhn Koh

(57) ABSTRACT

Provided is a method for preventing or treating a wound or scar comprising administering to a subject in need thereof a pharmaceutical composition comprising benzbromarone as an active ingredient, wherein benzbromarone inhibits the function of heat shock protein 47 (HSP47), or inhibits the accumulation of collagen by reducing collagen overproduction cells.

7 Claims, 15 Drawing Sheets

(56) References Cited

FOREIGN PATENT DOCUMENTS

| WO | 2008/112195 A1 | 9/2008 |
| WO | 2011/140173 A1 | 11/2011 |
| WO | 2019/112031 A1 | 6/2019 |

OTHER PUBLICATIONS

Mazali et al. "Use of Uric Acid-Lowering Agents Limits Experimental Cyclosporine Nephropathy", Nephron Exp Nephrol, 2012, 120:e12-e19.
Naitoh et al., "Fibrosis (hypertrophic scars—keloid)" on p. 122 of Regenerative Medicine, 2012, vol. 11, No. 2, pp. 120-124 with excerpt translation.
Prehm et al., "Inhibition of hyaluronan export from human fibroblasts by inhibitors of multidrug resistance transporters", Biochemical Pharmacology, 68 (2004) 1401-1410.
Takenaka, Paragraph 3 on p. 773 of Clinical in Dermatology, May 2020, vol. 62, No. 6, pp. 772-775 with excerpt translation.
Wakuda et al., "Is Hyperuricemia a Risk Factor for Arteriosclerosis? Uric Acid and Arteriosclerosis in Apolipoprotein E-Deficient Mice", Biol. Pharm. Bull., 37 (12) 1866-1871 (2014).

PHARMACEUTICAL COMPOSITION FOR PREVENTING OR TREATING WOUND OR SCAR, COMPRISING BENZBROMARONE

CROSS-REFERENCE TO RELATED APPLICATIONS

This application is a 371 of PCT/KR2021/017723 filed on Nov. 29, 2021, which claims the benefit of priority from Korean Patent Application No. 10-2020-0163975 filed on Nov. 30, 2020, the contents of each of which are incorporated herein by reference in its entirety.

FIELD

The present invention relates to a pharmaceutical composition for preventing or treating a wound or scar, and more specifically, to a pharmaceutical composition for preventing or treating a wound or scar comprising benzbromarone.

BACKGROUND

A keloid is a raised, erythematous, pruritic localized lesion with aggressive growth and fibrosis associated with excessive accumulation of extracellular matrix, particularly collagen overproduction in the skin. Numerous treatment modalities have been used for keloids, but none have been developed with consistent efficacy.

On the other hand, skin scars are raised scars caused by excessive collagen accumulation and are milder than keloids. Like keloids, they often form at the site of acne, piercings, cuts, and burns. Surgical removal and laser treatments are available to reduce the size of the scar, and medications include steroids and chemotherapy injections, but these are not standard treatments.

Heat shock protein 47 (HSP47) is a collagen-specific molecular chaperone residing in the endoplasmic reticulum (ER) and it has been found to be strongly associated with fibrosis. HSP47 is involved in the formation and transport of collagen from collagen precursors. The expression of HSP47 has been reported to be increased in fibrosis of various tissues, such as liver cirrhosis, pulmonary fibrosis, and glomerulosclerosis. Oligonucleotides against HSP47 have been experimentally reported to be effective against glomerulosclerosis, cirrhosis, and pulmonary fibrosis.

HSP47 has also been reported to be expressed in cancer cells, and increased expression of HSP47 has been reported to facilitate metastasis of many cancer cells, leading to increased mortality. It has also been reported that genetically inhibiting HSP47 expression suppresses cancer progression (Parveen A et. al., 2019).

OBJECT OF THE INVENTION

There is a close relationship between HSP47 and excessive accumulation of collagen, and excessive collagen accumulation and high expression of HSP47 in keloids and skin scars. These findings suggest that inhibition of HSP47 may be an effective and specific therapeutic target for the treatment of keloids, hypertrophic scars, and wounds. The technical problem to be solved in the present invention is to derive therapeutically active substances for the treatment of keloids, skin scars, and sores based on the inhibitory activity of HSP47.

The technical problem to be achieved by the present invention is not limited to the above-mentioned technical problem, and other technical problems not mentioned can be clearly understood by those skilled in the art from the description below.

SUMMARY

To achieve the above object, according to one aspect of the present invention, there is provided a pharmaceutical composition for preventing or treating a wound or scar, comprising benzbromarone as an active ingredient.

In one embodiment, treating a wound or scar may be via inhibition of HSP47 (Heat shock protein 47).

In one embodiment, treating a wound or scar may be via inhibition of collagen biosynthesis.

In one embodiment, the wound may be at least one selected from the group consisting of chronic wounds, acute wounds, surgical wounds, orthopedic wounds, trauma wounds, burn wounds and combat wounds.

In one embodiment, the scar may be at least one selected from the group consisting of keloid scars, hypertrophic scars, atrophic scars, and stretch marks.

In one embodiment, treating a wound or scar may be reduction of the area of the wound or scar.

In one embodiment, the pharmaceutical composition may further comprise a pharmaceutically acceptable diluent or carrier.

According to another aspect of the present invention, there is provided use of benzbromarone for the purpose of preventing or treating a wound or scar.

According to yet another aspect of the present invention, there is provided a method for preventing or treating a wound or scar, comprising administering to a subject in need thereof a therapeutically effective amount of benzbromarone.

According to the present invention, it has been confirmed that benzbromarone inhibits the function of heat shock protein 47 (HSP47) and inhibits the accumulation of collagen by reducing collagen overproduction cells, thereby it has been found that benzbromarone can be used for preventing or treating a wound or scar.

Thus, the composition comprising benzbromarone as an active ingredient of the present invention can be usefully employed in medical and pharmaceutical fields for preventing or treating a wound or scar.

The effects of the invention are not limited to those described above, but should be understood to include all effects that can be inferred from the detailed description of the present invention or from the composition of the invention as recited in the claims.

DETAILED DESCRIPTION OF THE INVENTION

The present invention provides a pharmaceutical composition for preventing or treating a wound or scar, comprising benzbromarone as an active ingredient.

Benzbromarone (BBR, INV-001a) is a chemical compound with the structure of Formula 1 below, and its IUPAC name is (3,5-dibromo-4-hydroxyphenyl)-(2-ethyl-1-benzofuran-3-yl)methanone (molecular weight 423.91).

<Formula 1>

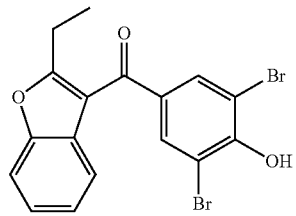

Evaluation of benzbromarone for inhibition of heat shock protein 47 (HSP47) activity showed an $IC_{50}$ of 132.7 μM, confirming that benzbromarone exhibits HSP47 inhibitory activity. Regarding the fibrosis inhibition activity in tissue cells, benzbromarone inhibited fibrosis in hepatic stellate cells and lung epithelial cells and, in particular, inhibited fibrosis in skin fibroblasts, reducing the area of skin wounds and scars, confirming its activity in the treatment of wounds or scars. In an animal model of liver fibrosis induction, benzbromarone significantly reduced plasma ALT and bilirubin, inhibited fibrosis in liver tissue by histochemistry, and reduced the content of 4-hydroxyproline in liver tissue, thereby reducing fibrosis-induced collagen deposition, confirming that benzbromarone has inhibitory effect to collagen biosynthesis.

The present invention also provides a use of benzbromarone for the purpose of preventing or treating a wound or scar.

The present invention also provides a method for preventing or treating a wound or scar, comprising administering to a patient in need thereof a therapeutically effective amount of benzbromarone.

Figure 6A:
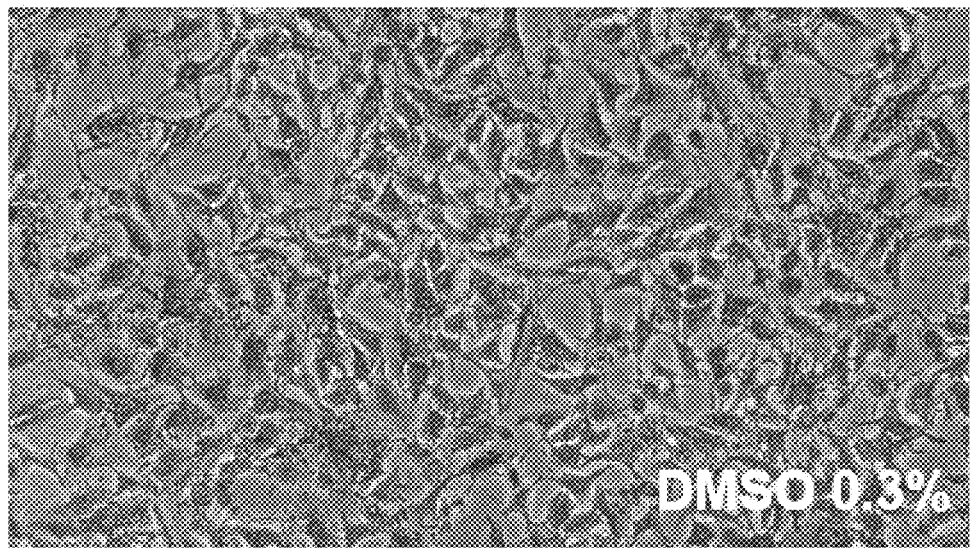
FIG. 6A and FIG. 6B show Sirius red staining of cells treated with 10 ng/ml TGF-β1 to induce fibrosis (FIG. 6A) and co-treated with benzbromarone (BBR, 30 μM) (FIG. 6B) in A549 lung epithelial cells.
Figure 6B:
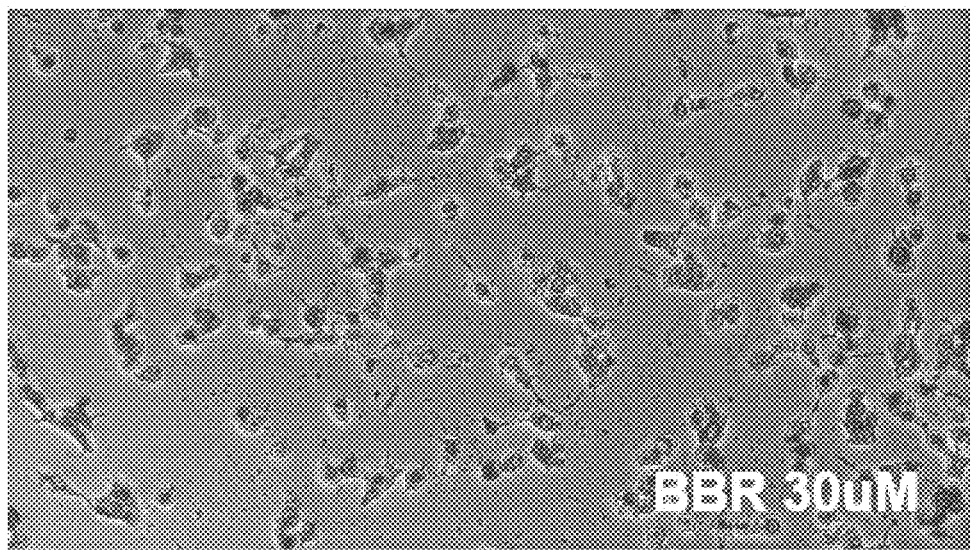
Figure 7:
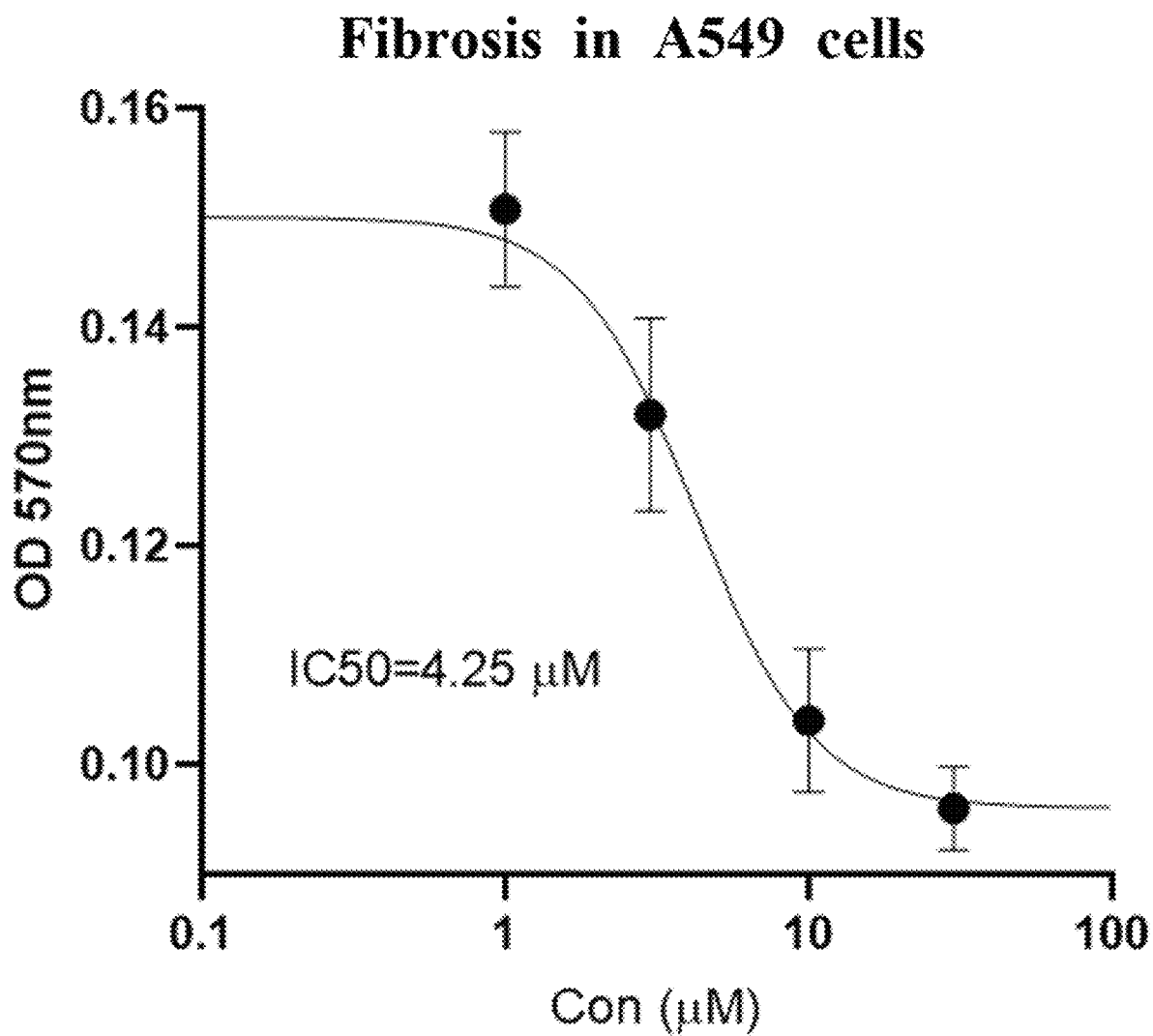
FIG. 7 shows the fibrosis inhibition [OD (570 nm)] at each concentration of benzbromar one (BBR) in lung epithelial cells A549.

HSP47 has been reported to be expressed in cancer cells, and increased expression of HSP47 has been shown to facilitate metastasis of cancer cells through the accumulation of collagen, which is necessary for cancer cell growth. In A549 lung epithelial cell carcinoma, inhibition of HSP47 by benzbromarone treatment resulted in inhibition of collagen accumulation (FIGS. 6A, 6B and 7).

In the present invention, said wound may be at least one selected from the group consisting of chronic wounds, acute wounds, surgical wounds, orthopedic wounds, trauma wounds, burn wounds, and combat wounds.

In the present invention, said scar may be at least one selected from the group consisting of keloid scars, hypertrophic scars, atrophic scars, and stretch marks that form on the skin following a wound.

In one embodiment, treating the said wound or scar may mean a reduction of the area of the wound or scar.

In one embodiment, said pharmaceutical composition may further comprise a pharmaceutically acceptable diluent or carrier.

Specifically, the pharmaceutical composition of the present invention may include pharmaceutically acceptable carriers, each of which may be formulated according to conventional methods in the form of oral formulations such as powder, granules, tablets, capsules, suspensions, emulsions, syrups, aerosols; topicals; suppositories; and sterile injectable solutions. The pharmaceutically acceptable carriers include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinyl pyrrolidone, water, methylhydroxybenzoate, propylhydroxybenzoate, talc, magnesium stearate, mineral oil and the like. They also include diluents or excipients such as fillers, bulking agents, binders, wetting agents, disintegrating agents, and surfactants. Oral solid dosage forms include tablets, pills, powders, granules, capsules, and the like, which may include at least one excipient, such as starch, calcium carbonate, sucrose or lactose, gelatin, and the like, and may include lubricants such as magnesium stearate and talc. Oral liquid formulations include suspensions, inclusions, emulsions, syrups, and the like, and may include diluents such as water and liquid paraffin, wetting agents, sweeteners, flavorings, preservatives, and the like. Parenteral preparations include sterile aqueous solutions, non-aqueous solvents, suspensions, emulsions, lyophilized preparations, and suppositories. Non-aqueous solvents and suspensions include propylene glycol, polyethylene glycol, vegetable oils such as olive oil, and injectable esters such as ethylolates. Substrates for suppositories may include witepsol, macrogol, tween 61, cacao gum, laurin gum, and glycerogelatin.

The dose of benzbromarone in the pharmaceutical compositions of the present invention depends on the condition and weight of the patient, the extent of the disease, the formulation, the route and duration of administration, but may be suitably selected by one of those skilled in the art. For example, benzbromarone may be administered at a dose of 0.0001 to 1000 mg/kg per day, preferably 0.01 to 1000 mg/kg per day, and said dose may be administered once or in several divided doses per day. Furthermore, the pharmaceutical composition of the present invention may comprise benzbromarone from 0.001 to 90% by weight, based on the total weight of the composition.

The pharmaceutical composition of the present invention may be administered to mammals such as rats, mice, livestock, and humans by various routes, for example, orally, intraperitoneally, rectally, by intravenous, intramuscular, subcutaneous, intrauterine dural, or intracerebroventricular injection.

Hereinafter, the present disclosure is described in considerable detail with examples to help those skilled in the art understand the present disclosure. However, the following examples are offered by way of illustration and are not intended to limit the scope of the invention.

EXAMPLES

Example 1. Experiment (1) Compound Tested

The following experiments were performed on Benzbromarone, IUPAC name (3,5-dibromo-4-hydroxyphenyl)-(2-ethyl-1-benzofuran-3-yl)methanone (molecular weight 423.91, purchased from TCI [JP]), which has the structure of the following formula 1.

<Formula 1>

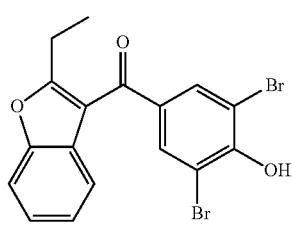

(2) Evaluation of HSP47 Activity

Fibrils were formed by adding 180 ul of phosphate-buffered saline (PBS, pH 7.4) solution to 20 ul of collagen dissolved in acidic solution (collagen solution, UK), which was measured at a wavelength of 340 nm. HSP47 (GenScript US) was added at a concentration of 9.45 μg/ml to evaluate HSP47 activity as the degree to which it inhibits fibril formation. Test compound was added with concentrations of 100 μM to 1 μM and the inhibitory activity of HSP47 was calculated as a percentage.

(3) Sirius Red Assay

Hepatic stellate LX-2 (Elabscience CH), lung epithelial A549 (ATCC US), liver stellate T6 (Elabscience, CH), or skin KEL FIB (ATCC, US) cells were cultured in 24-well tissue culture plates for 18 hours, followed by TGF-beta 10 ng/ml treatment, and then incubated with test compounds for 24 hours. Cells were washed with PBS, fixed with Bouin's solution, and washed twice with distilled water. The fixed cells were stained with Sirius red for 2 hours to observe cellular morphological changes, and then washed with 0.01 N HCl solution. Collagen-bound Sirius red was extracted with 0.1 N NaOH solution, which was then quantified at a wavelength of 570 nm. The inhibitory efficacy of each compound on collagen production was shown as a percentage.

(4) Test with Carbon Tetrachloride-Induced Liver Fibrosis Model in Mice $CCl_4$ was administered intraperitoneally at 50 uL (1:1 corn oil) per mouse three times a week for 4 weeks, and the test compound was suspended in 0.5% methylcellulose and administered orally at a dose of 5 ml/kg daily. As a positive control, obeticholic acid (Medkoo, US) was administered at a dose of 30 mg/kg. Body weight was measured once a week during the study period. 28 days after $CCl_4$ administration, rats were inhalationally anesthetized with ether, and once anesthesia was confirmed, they were laparotomized and blood was drawn using a syringe from the posterior vena cava, and then the abdominal aorta and posterior vena cava were cut to exsanguinate/death. Blood was separated into serum and blood biochemical tests were performed. The liver was removed and weighed, the right lobe was fixed in 10% neutral buffered formalin solution, and the left lobe was divided in half and quick-frozen in liquid nitrogen. The quick-frozen samples were stored in an ultra-low temperature freezer set below −70° C. and used for 4-Hydroxyproline assay.

The fixed tissues were subjected to the usual tissue processing procedures such as cutting, dehydration, paraffin embedding, and sectioning to prepare specimens for histopathological examination. Hematoxylin & Eosin (H&E) and Picrosirius red staining were performed, and histopathological changes were observed using optical microscope (Olympus BX53, Japan), and the area of fibrosis was analyzed.

(5) Evaluation of Efficacy in Inhibiting Burn-Induced Skin Scarring

Yucatan minipigs that had been fasted for at least 8 hours were anesthetized using xylazine hydrochloride, midazolam, and propofol. After removing the hair on the trunk and back, the test area was disinfected with povidone iodine solution. Burns were induced by contacting the test area with a 400-gram stainless steel weight for 40 seconds. Burns were applied 2 cm from the spine and 4 cm apart between burn sites. The burn area should not exceed 3.5% of the total animal area. 15 days after burning, the scab was removed and the test compound was applied to the wounds once daily. At 45 days after burn induction, autopsy was performed, and the wounds were fixed in formalin solution and H&E staining was performed to measure the thickness of the dermal layer.

The test compound was suspended in propylene glycol (Yakuri pure chemicals, Japan) and made into a homogeneous suspension using an ultrasonic cleaner, which was then diluted in lanolin (Merck, USA) and petroleum jelly (Merck, USA) under 60° C. water bath to prepare an ointment. Each component of the prepared ointment is 1% (w/w) of the test compound, 20% (w/w) of propylene glycol, 15% (w/w) of lanolin, and 64% (w/w) of vaseline.

2. Results (1) Inhibition of HSP47 Function

Figure 1:
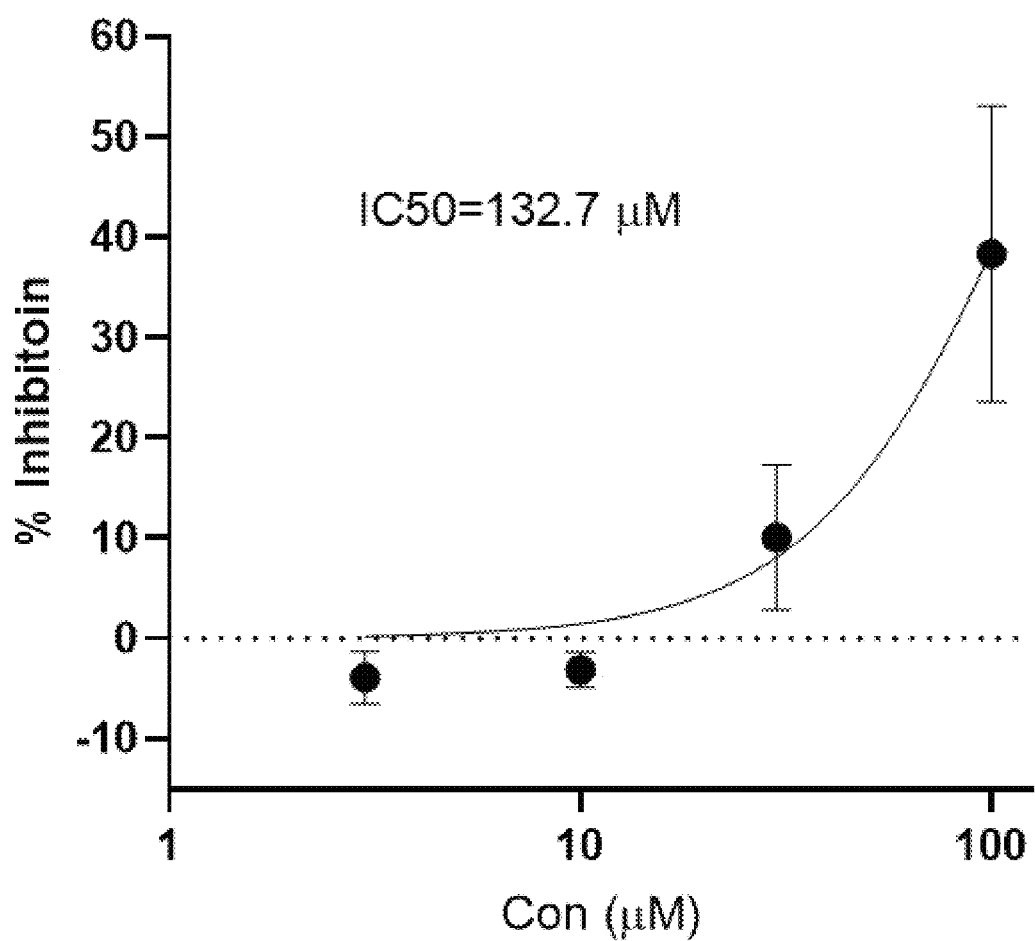
FIG. 1 shows inhibition percentage (% inhibition) of HSP47 function by benzbromarone at each concentration.

The OD measured when collagen was placed in PBS buffer (pH 7.4) to form fibrils at 37° C. was taken as 100%, and the OD measured when HSP47 and collagen were placed together to form fibrils was taken as 0%. The percentage of inhibition of HSP47 by the test compound at each concentration was measured. $IC_{50}$ values were calculated using Prism software (Graphpad, USA). Measuring the extent of HSP47 inhibition with benzbromarone, an $IC_{50}$ of 132.7 μM was obtained (FIG. 1).

(2) Inhibition of Hepatic Stellate Cell LX-2 Fibrosis

Figure 2A:
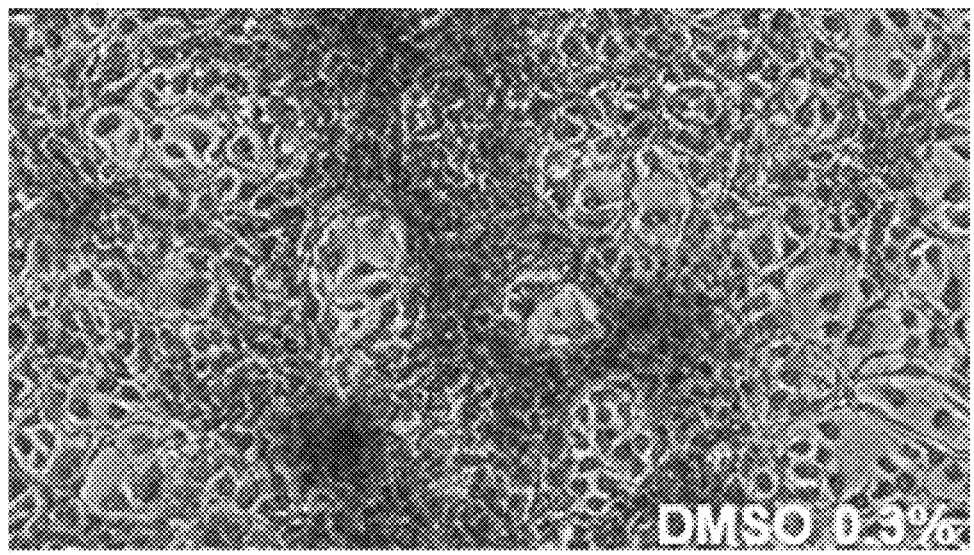
FIG. 2A and FIG. 2B show Sirius red staining of cells treated with 10 ng/ml TGF-$\beta$1 to induce fibrosis (FIG. 2A) and co-treated with benzbromarone (BBR, 30 $\mu$M) (FIG. 2B) in LX-2 hepatic stellate cells.
Figure 2B:
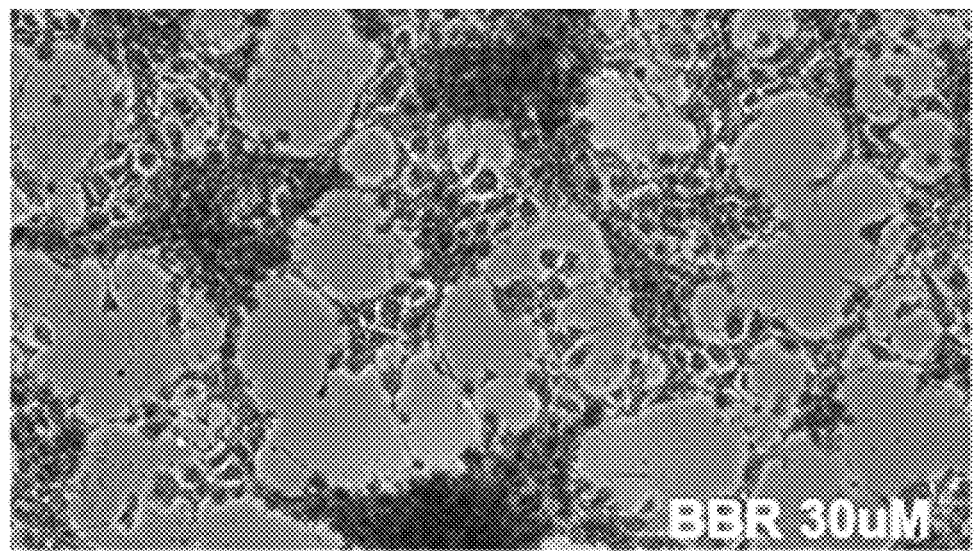
Figure 3:
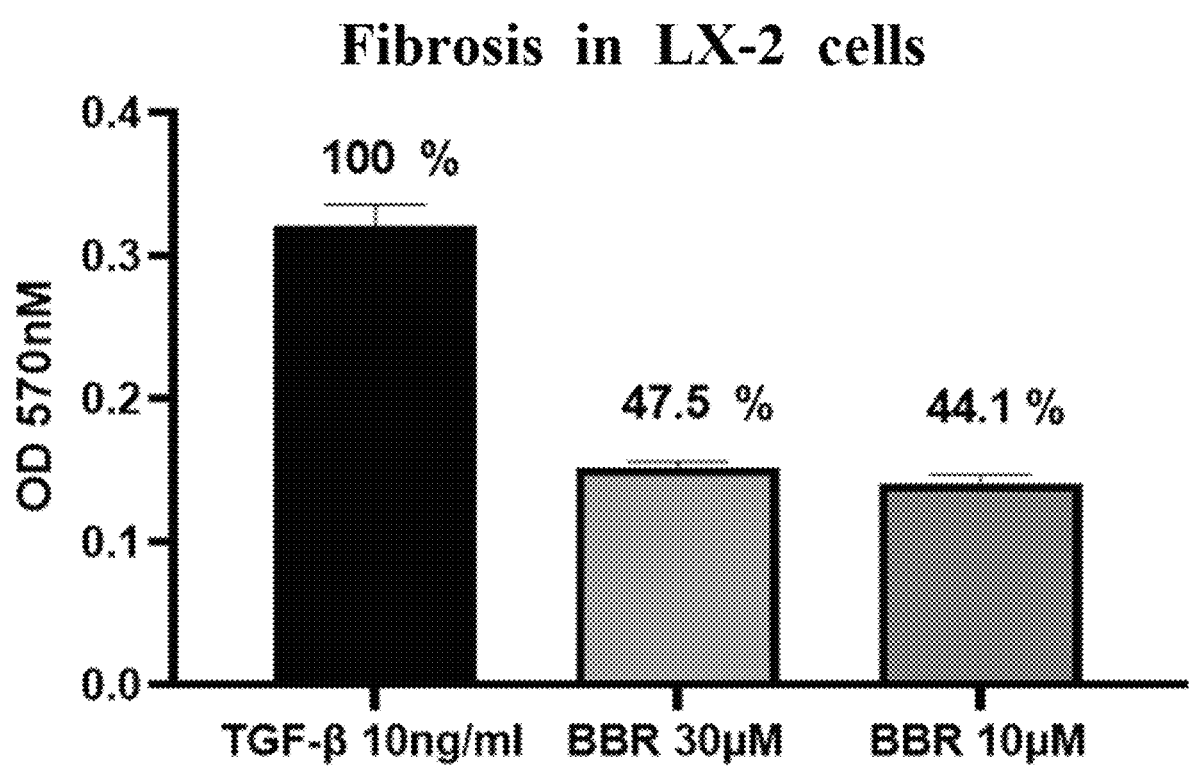
FIG. 3 is results of cells treated with 10 ng/ml TGF-$\beta$1 to induce fibrosis and co-treated with benzbromarone (BBR, 30 $\mu$M, 10 $\mu$M) in LX-2 hepatic stellate cells.

Hepatic stellate cell LX-2 was treated with 10 ng/ml TGF-β1 (Gibco, US) to induce fibrosis, and the benzbromarone (BBR) treatment group was treated with TGF-β1 and benzbromarone (BBR) simultaneously. The extent of fibrosis inhibition was observed by fixing the cells and staining them with Sirius Red, a collagen-specific stain, to observe morphological changes (FIG. 2A, 2B), and quantified by extracting Sirius Red with 0.1 N NaOH solution (FIG. 3). As shown in the Sirius Red staining results (FIG. 2A, 2B), fibrosis was reduced in hepatic stellate cells LX-2 treated with M of benzbromarone (BBR), and the degree of fibrosis was significantly reduced compared to the TGF-β1 treatment group (FIG. 3).

(3) Inhibition of Hepatic Stellate Cell T6 Fibrosis

Figure 4A:
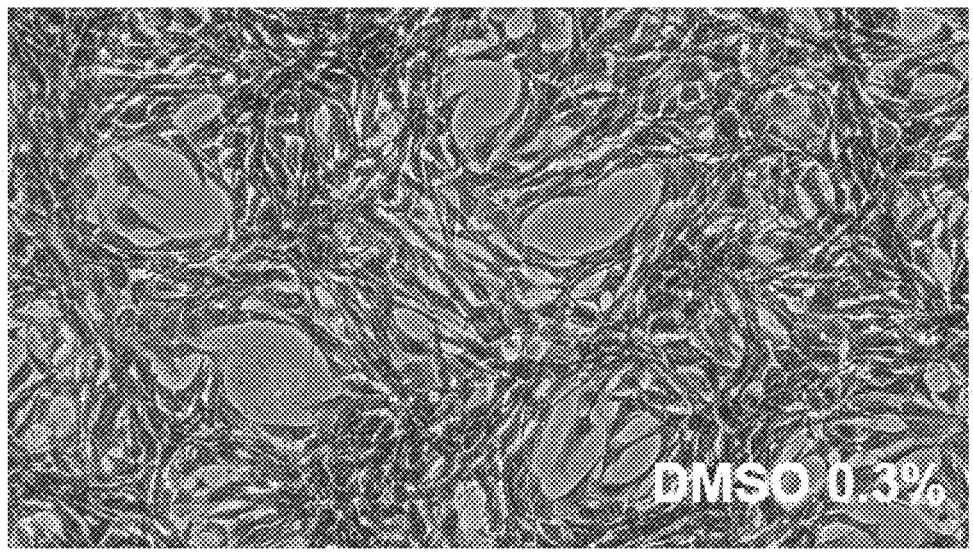
FIG. 4A and FIG. 4B show Sirius red staining of cells treated with 10 ng/ml TGF-$\beta$1 to induce fibrosis (FIG. 4A) and co-treated with benzbromarone (BBR, 30 $\mu$M) (FIG. 4B) in T6 hepatic stellate cells.
Figure 4B:
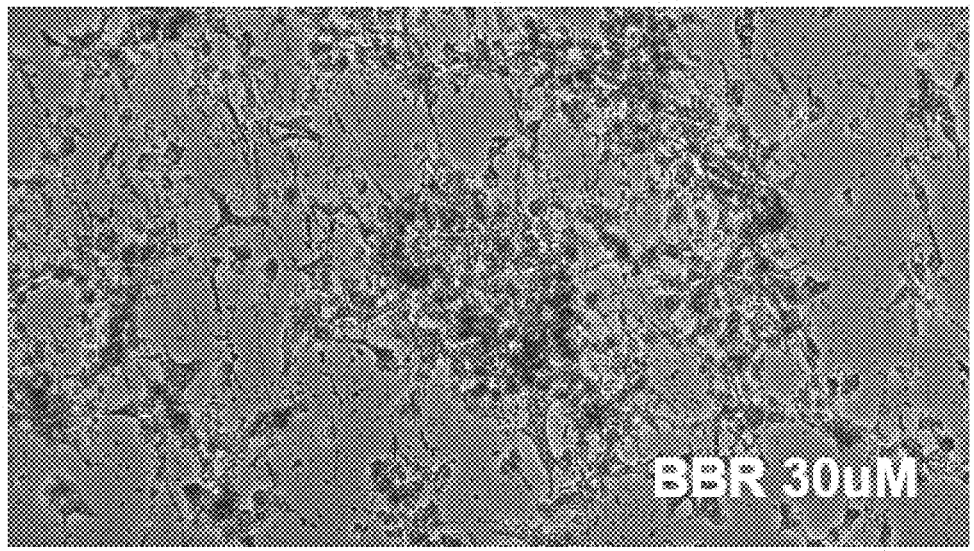
Figure 5:
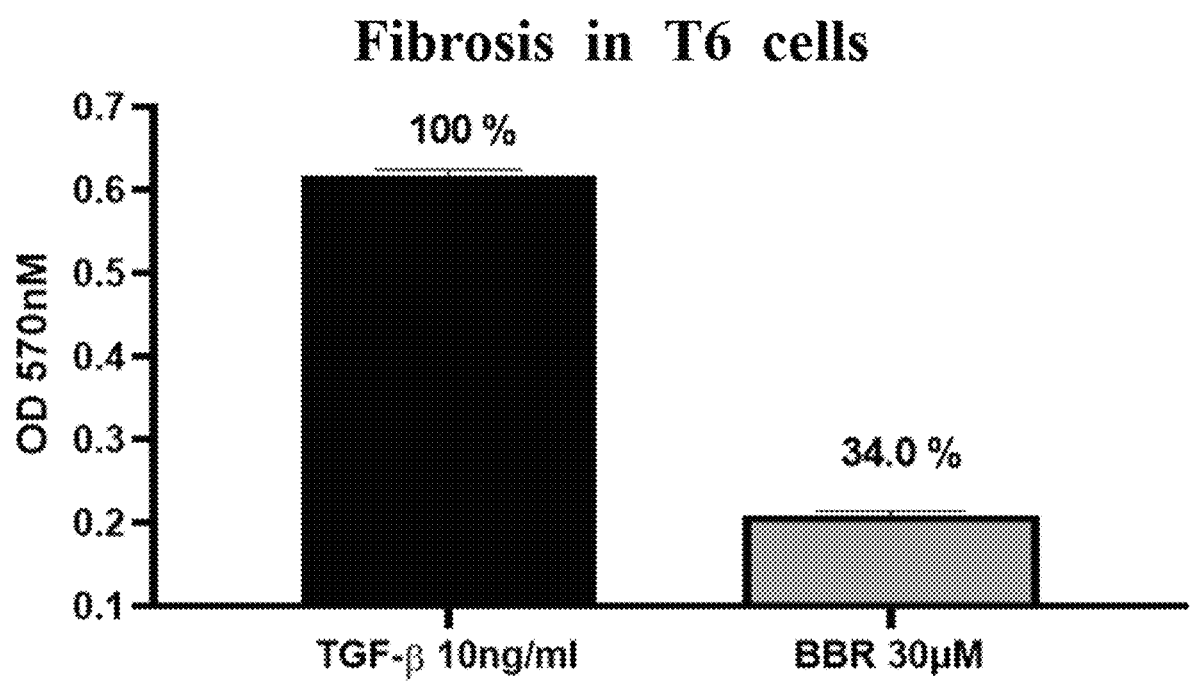
FIG. 5 is results of cells treated with 10 ng/ml TGF-β1 to induce fibrosis and co-treated with benzbromarone (BBR, 30 μM) in T6 hepatic stellate cells.

Hepatic stellate cell T6 was treated with 10 ng/ml TGF-β1 to induce fibrosis, and the test compound was treated simultaneously. The extent of fibrosis inhibition was observed by fixing the cells and staining them with Sirius Red, a collagen-specific stain, to observe morphological changes (FIG. 4A, 4B), and quantified by extracting Sirius Red with 0.1 N NaOH solution (FIG. 5). As shown in the Sirius Red staining results (FIG. 4A, 4B), fibrosis was reduced in hepatic stellate cell T6 treated with 30 μM of benzbromarone (BBR), and the degree of fibrosis was significantly reduced compared to the TGF-β1 treatment group (FIG. 5).

(4) Inhibition of Lung Epithelial Cell A549 Fibrosis

Lung epithelial cells A549 were treated with 10 ng/ml TGF-β1 to induce fibrosis, and the test compound was treated simultaneously. The extent of fibrosis inhibition was observed by fixing the cells and staining with Sirius Red, a collagen-specific stain, to observe morphological changes (FIG. 6A, 6B), and quantified by extracting Sirius Red with 0.1 N NaOH solution (FIG. 7). As shown in the Sirius Red staining results (FIG. 6A, 6B), fibrosis was reduced in lung epithelial cells A549 treated with 30 μM of benzbromarone (BBR). The extent of fibrosis inhibition in lung epithelial cells A549 was measured at each concentration of benzbromarone (BBR), and $IC_{50}$ of 4.25 μM was obtained (FIG. 7).

(5) Inhibition of Dermal Fibroblast KEL FIB Fibrosis

Figure 8A:
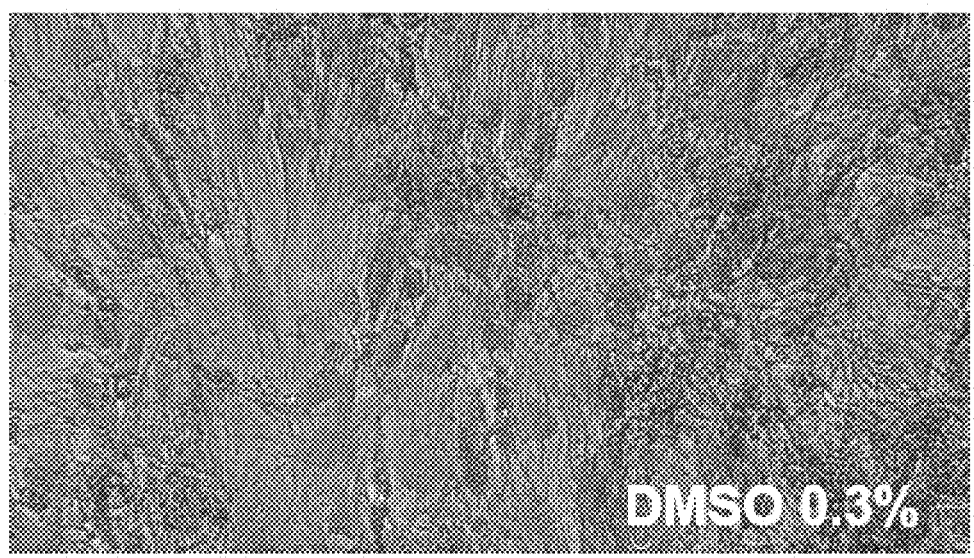
FIG. 8A and FIG. 8B show Sirius red staining of cells treated with 10 ng/ml TGF-β1 to induce fibrosis (FIG. 8A) and co-treated with benzbromarone (BBR, 30 μM) (FIG. 8B) in KEL FIB cells isolated from keloid patients.
Figure 8B:
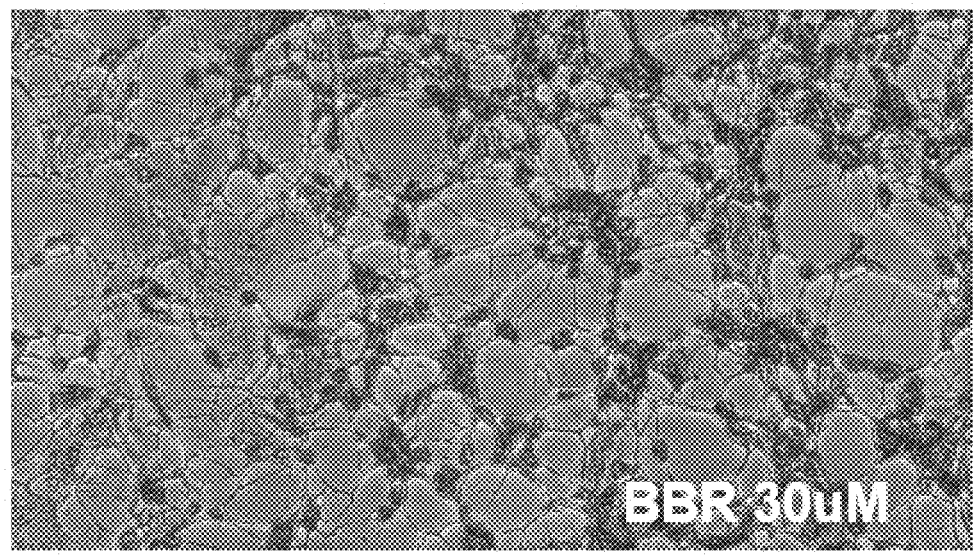
Figure 9:
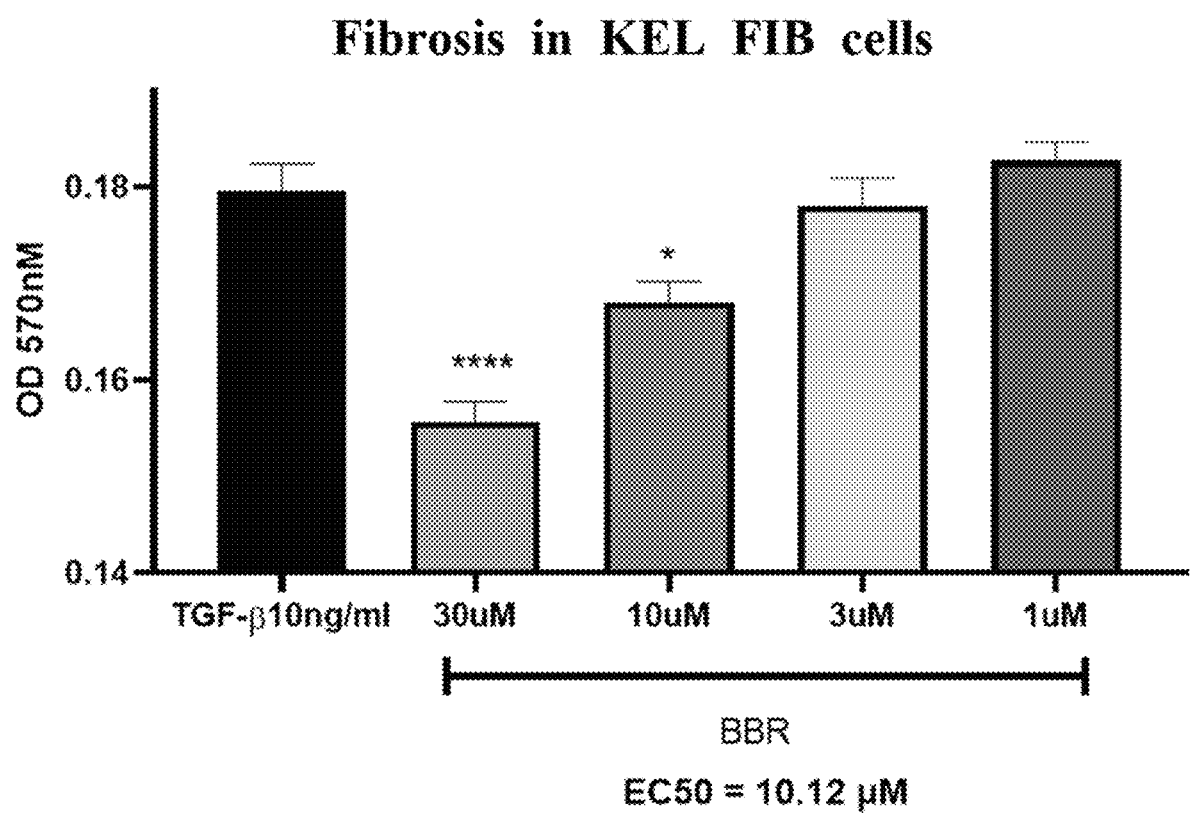
FIG. 9 shows the inhibitory effect on fibrosis at each concentration of benzbromarone (BBR) in KEL FIB cells isolated from keloid patients.

KEL FIB cells (ATCC, USA) isolated from keloid patients were treated with 10 ng/ml TGF-β1 to induce fibrosis, and the test compound was treated simultaneously. The extent of fibrosis inhibition was observed by fixing the cells and staining them with Sirius Red, a collagen-specific stain, to observe morphological changes (FIG. 8A, 8B), and quantified by extracting Sirius Red with 0.1 N NaOH solution (FIG. 9). As shown in the Sirius Red staining results (FIG. 8A, 8B), fibrosis was reduced in KEL FIB cells treated with 30 μM of benzbromarone (BBR). The extent of fibrosis inhibition in KEL FIB cells was measured at each concentration of benzbromarone (BBR) treated, and the fibrosis inhibitory effect began to appear at 3 μM, significantly inhibiting from 10 μM (FIG. 9).

(6) Analysis of Plasma ALT and Bilirubin

Figure 10A:
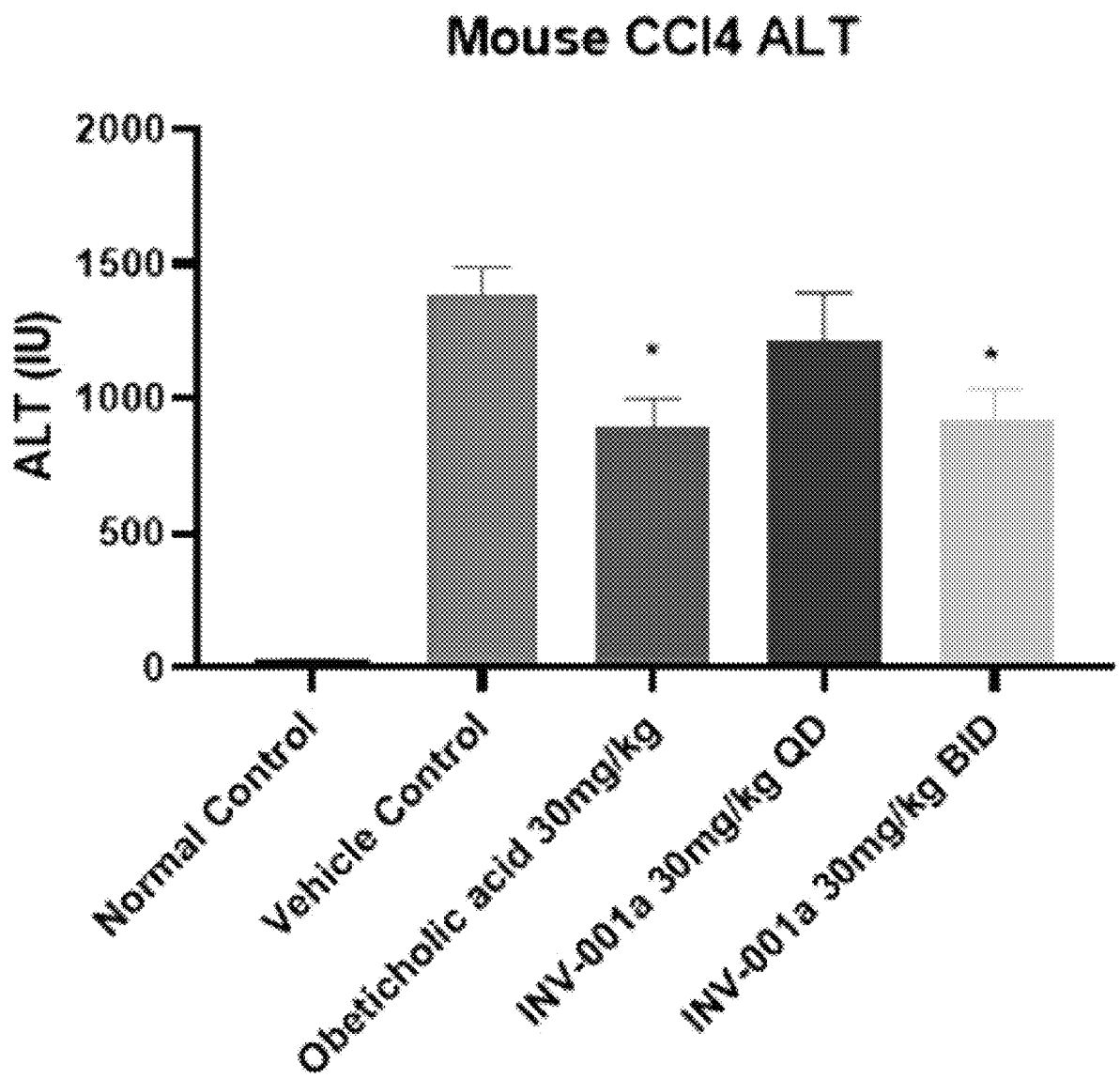
FIG. 10A and FIG. 10B show the result of plasma alanine aminotransferase (ALT) (FIG. 10A) and bilirubin levels (FIG. 10B) in a carbon tetrachloride-induced Hepatic Fibrosis model.
Figure 10B:
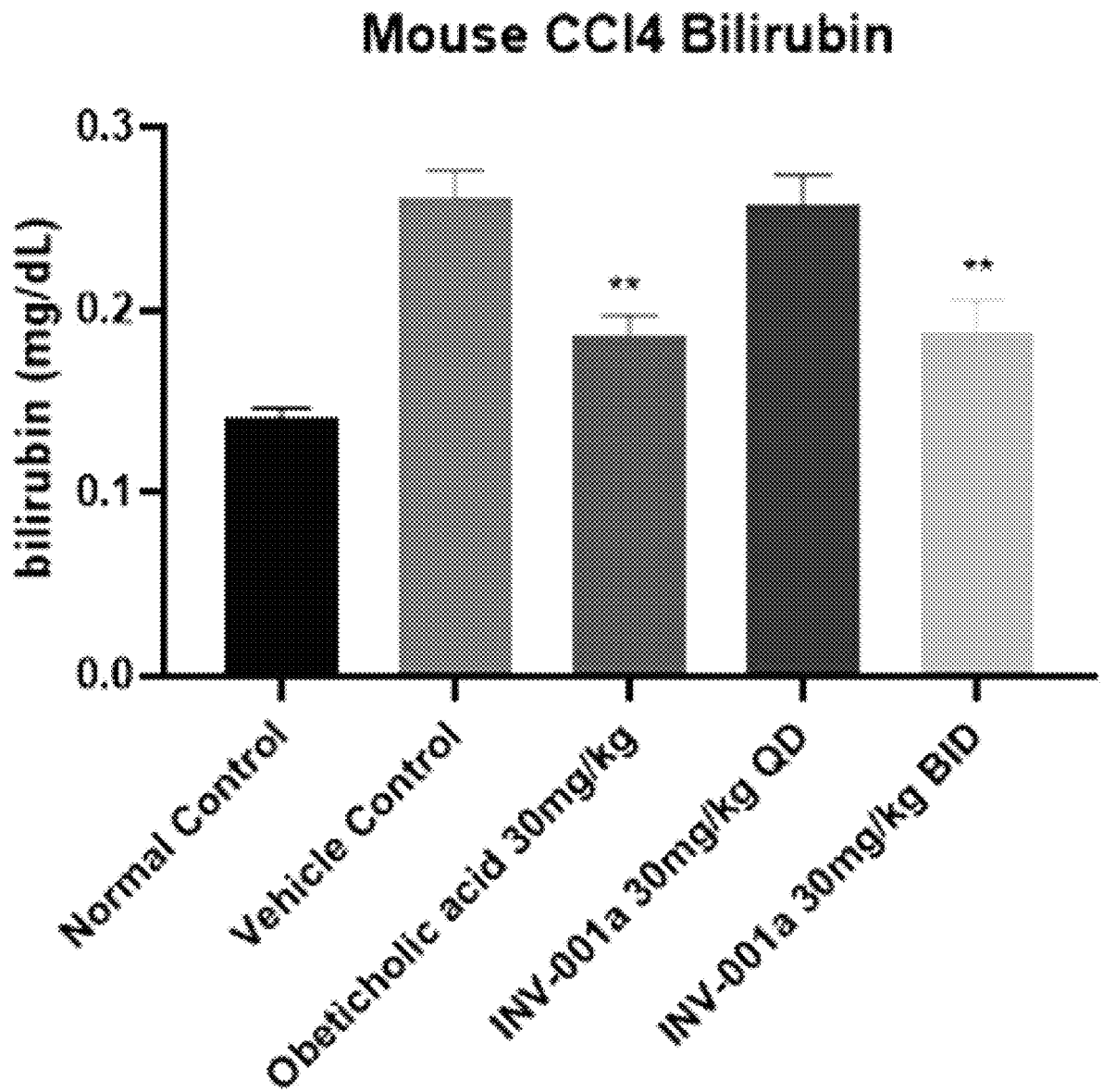

To determine the extent of carbon tetrachloride-induced liver tissue damage and liver function, plasma alanine aminotransferase (ALT) and bilirubin levels were analyzed in the plasma collected from autopsy using a blood biochemistry analyzer (7180 Hitachi, Japan). Statistically significant decreases in ALT and bilirubin were observed in the BBR twice-a-day treatment group (FIG. 10A, 10B).

(7) Analysis of Liver Fibrosis Tissue Specimens

Figure 11:
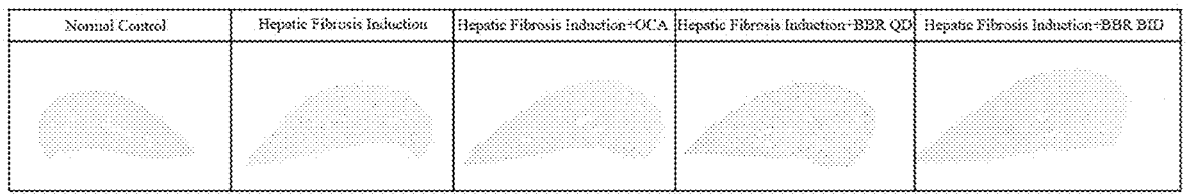
FIG. 11 shows Sirius Red staining results of the livers from each group of mice in a carbon tetrachloride-induced Hepatic Fibrosis model [Normal Control, Hepatic Fibrosis Induction (Vehicle Control), Hepatic Fibrosis Induction+ OCA (Obeticholic acid), Hepatic Fibrosis Induction+BBR QD (once a day), Hepatic Fibrosis Induction+BBR BID (twice a day)].
Figure 12:
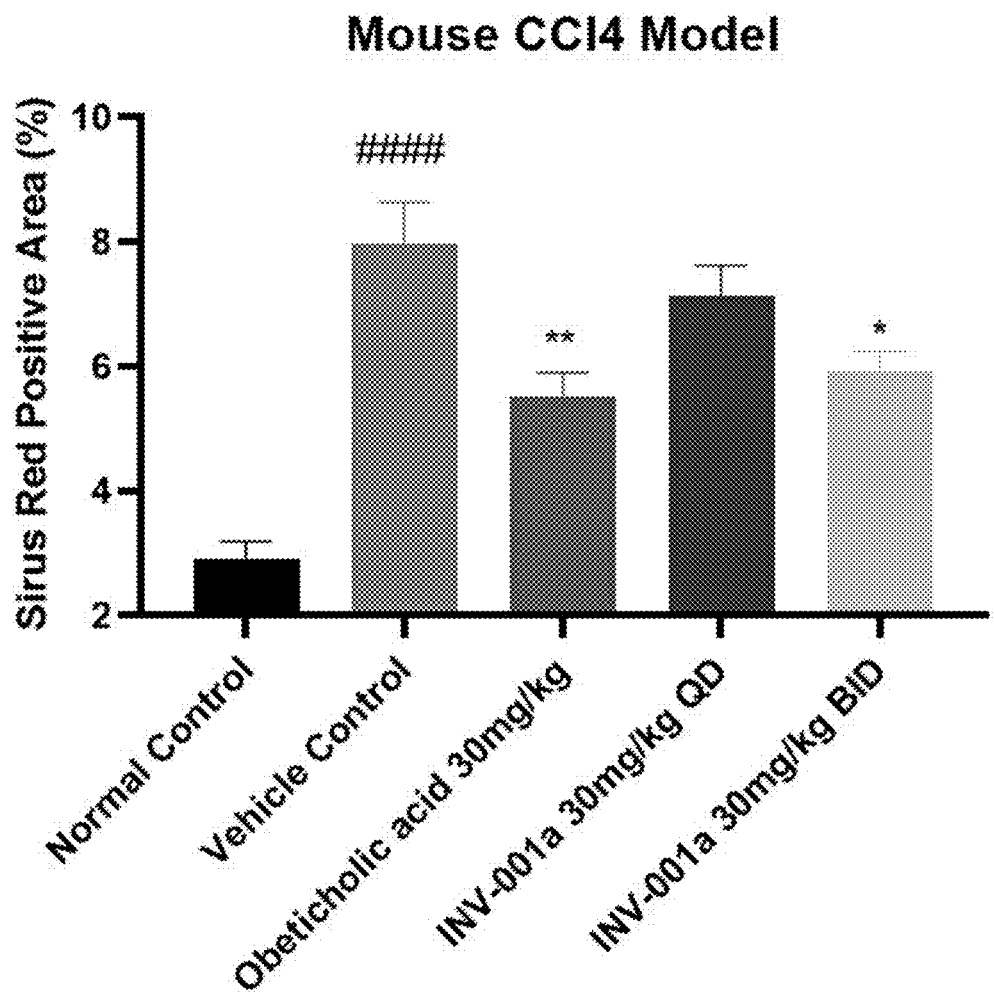
FIG. 12 shows the analysis results of fibrosis area of the livers from each group of mice in a carbon tetrachloride-induced Hepatic Fibrosis model [Normal Control, Hepatic Fibrosis Induction (Vehicle Control), Hepatic Fibrosis Induction+OCA (Obeticholic acid, 30 mg/kg), Hepatic Fibrosis Induction+BBR QD (INV-001a 30 mg/kg QD), Hepatic Fibrosis Induction+BBR BID (INV-001a 30 mg/kg BID)].

Fibrosis area analysis was performed to determine the extent of fibrosis in liver tissue (FIG. 11, FIG. 12), and BBR twice-a-day treatment group showed a comparable result with fibrosis inhibition as the obeticholic acid (OCA) treatment group.

(8) Analysis of 4-Hydroxy Proline in Liver Tissue

Figure 13:
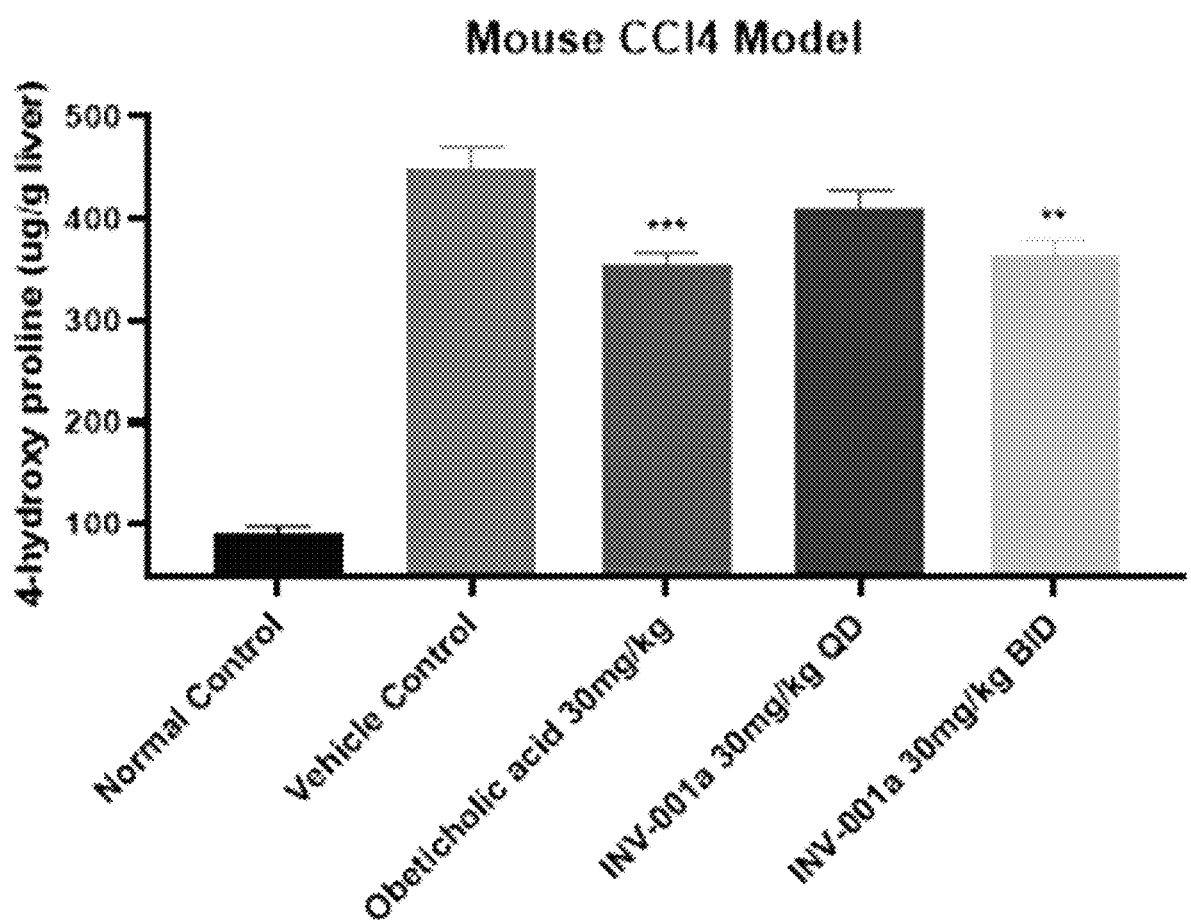
FIG. 13 shows the analysis of the content of 4-hydroxy-proline in collagen in a carbon tetrachloride-induced injured liver tissue [Normal Control, Hepatic fibrosis induction (Vehicle Control), Hepatic fibrosis induction+OCA (Obeticholic acid 30 mg/kg), Hepatic fibrosis induction+BBR QD (INV-001a 30 mg/kg QD), Hepatic fibrosis induction+BBR BID (INV-001a 30 mg/kg BID)].

As liver fibrosis progresses, collagen is deposited in liver tissue. The content of 4-hydroxyproline in collagen in a carbon tetrachloride-induced injured liver tissue was analyzed to determine the extent of fibrosis. The content of 4-hydroxyproline was statistically significantly reduced in the BBR twice-a-day treatment group (FIG. 13).

(9) Evaluation of the Efficacy of Reducing Wounds or Scars

Figure 14A:
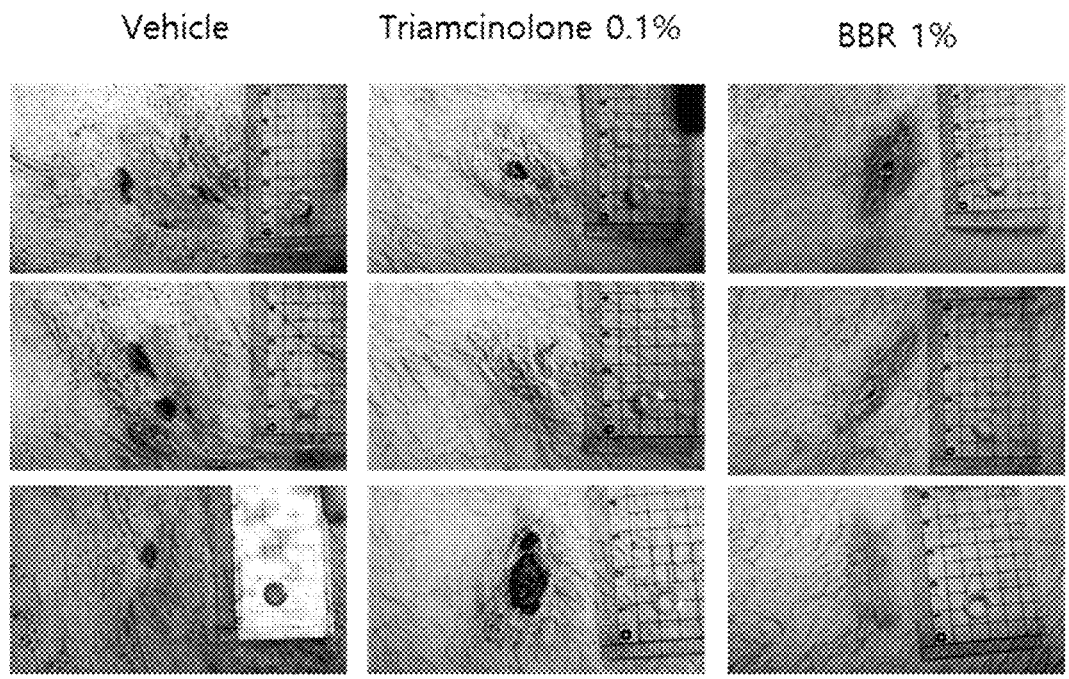
FIG. 14A and FIG. 14B show photographs of burn-induced scarring in minipigs (n=3) (FIG. 14A) and the area of each scarring site measured in cm$^2$ (FIG. 14B).
Figure 14B:
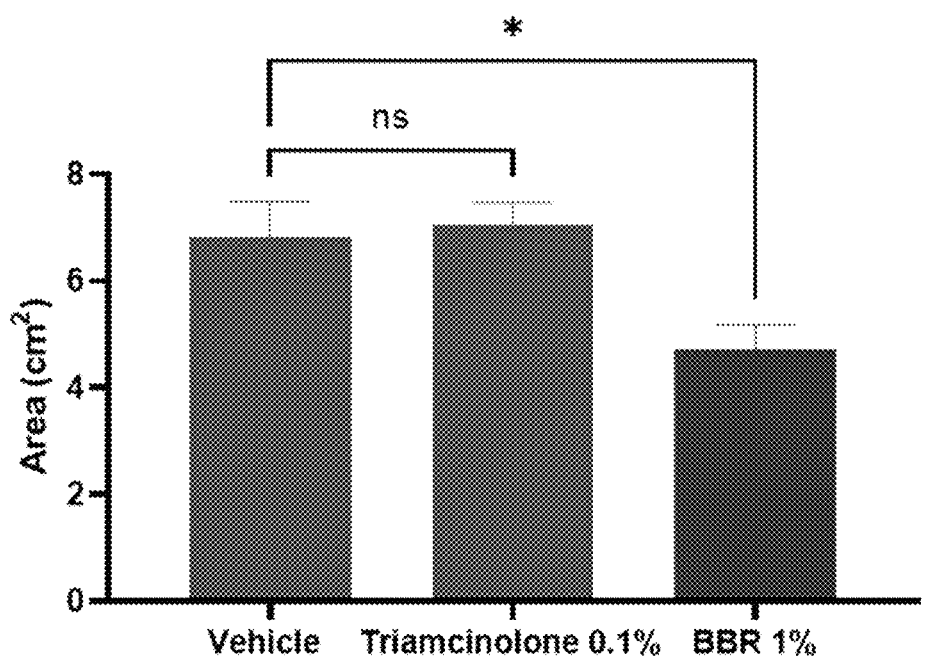

The scarring areas of the burn-induced minipigs were photographed at day 45 of burn induction and were shown in FIG. 14A. As shown in FIG. 14A, the scar size and wound extent of the BBR treatment group (BBR 1%) were significantly reduced compared to the control group (Vehicle), and the scar extent was also reduced compared to the positive control group, the steroidal triamcinolone treatment group (Triamcinone, 0.1%, Dongguang Pharmaceutical). Furthermore, the scar size was calculated as an area in $cm^2$ and shown in FIG. 14B. The reduction of scar size and wound in the BBR treatment group (BBR 1%) was clearly shown numerically.

Figure 15A:
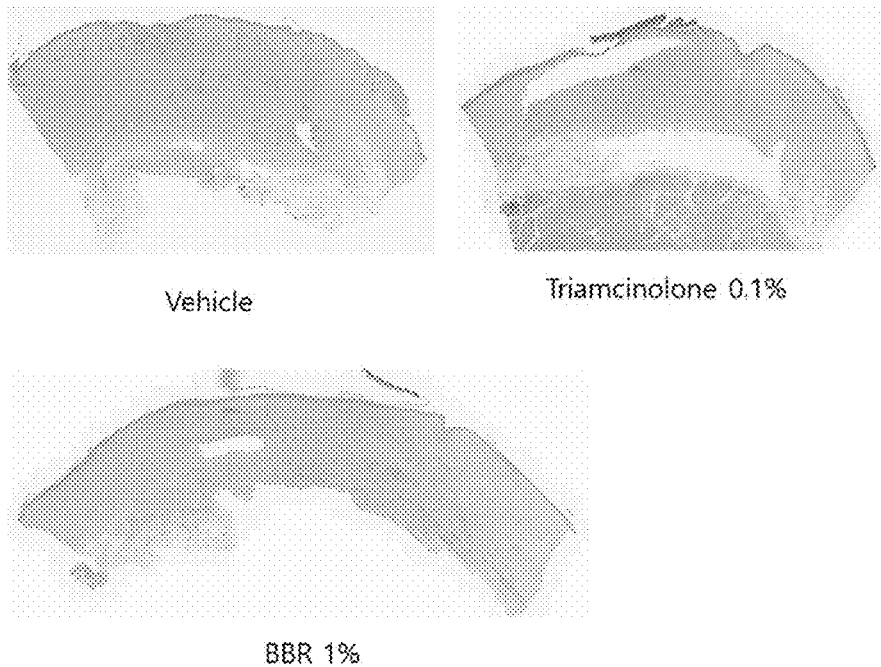
FIG. 15A and FIG. 15B are a photograph of a slide of tissue from the scarred area of a minipig induced by the burn of FIG. 14A and stained with Hematoxylin & Eosin (H&E) (FIG. 15A), and a graph of the scar tissue thickness measured in milimeters (mm) (FIG. 15B), confirming the hypertrophy of the dermal layer.
Figure 15B:
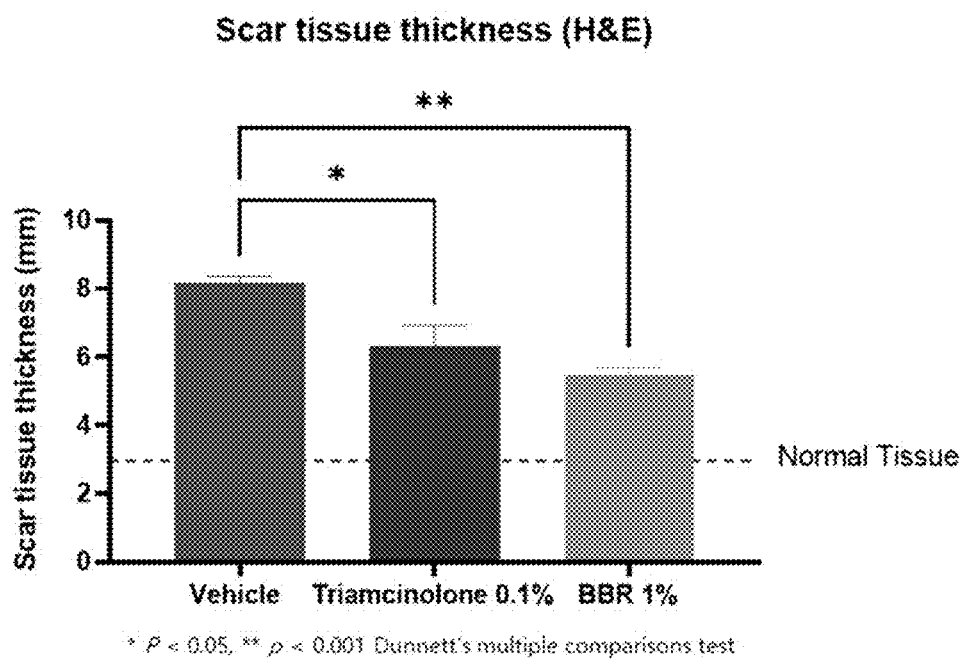

In addition, the results of the scanning image of the scar tissue slide were shown in FIG. 15A, and the extent of hypertrophy of the dermal layer was lower in the BBR treatment group (BBR 1%) than in the other groups. Also, the numerical measurement of the hypertrophy of the dermis layer was shown in FIG. 15B, and the hypertrophy of the dermis layer was the lowest in the BBR treatment group (BBR 1%).

The foregoing description of the invention is for illustrative purposes only, and it will be readily apparent to those skilled in the art to which the invention belongs that varying substitutions and modifications may be made to the invention disclosed herein without departing from the spirit of the invention or essential features of the invention. It should therefore be understood that the embodiments described above are for the purpose of illustration of the invention only and are not intended in any way to limit the scope of the present invention. For example, each of the components described in a single form may also be implemented in a distributed manner, and similarly, components described as distributed may also be implemented in a combined form.

The scope of the invention is indicated by the following patent claims. The meaning and scope of the patent claims and all modifications or variations derived from their equivalents are considered to be falling within the scope of the invention.

What is claimed is:

1. A method for treating a wound or scar, comprising: administering to a subject in need thereof a pharmaceutical composition comprising a therapeutically effective amount of benzbromarone, and thereby treating a wound or scar.

2. The method of claim 1, wherein the composition further comprises a pharmaceutically acceptable diluent or carrier.

3. The method of claim 1, wherein the treating is via inhibiting HSP47 (Heat shock protein 47).

4. The method of claim 1, wherein the treating is via inhibiting collagen biosynthesis.

5. The method of claim 1, wherein the wound is selected from the group consisting of chronic wounds, acute wounds, surgical wounds, orthopedic wounds, trauma wounds, burn wounds, combat wounds, and combinations thereof.

6. The method of claim 1, wherein the scar is selected from the group consisting of keloid scars, hypertrophic scars, atrophic scars, stretch marks, and combinations thereof.

7. The method of claim 1, wherein the composition reduces the area of the wound or scar.

* * * * *